United States Patent
Eversull et al.

(10) Patent No.: US 9,629,978 B2
(45) Date of Patent: Apr. 25, 2017

(54) CATHETERS WITH INTERMEDIATE LAYERS AND METHODS FOR MAKING THEM

(71) Applicants: Christian S. Eversull, Palo Alto, CA (US); Stephen A. Leeflang, Sunnyvale, CA (US)

(72) Inventors: Christian S. Eversull, Palo Alto, CA (US); Stephen A. Leeflang, Sunnyvale, CA (US)

(73) Assignee: CLPH, LLC, Palo Alto, CA (US)

( * ) Notice: Subject to any disclaimer, the term of this patent is extended or adjusted under 35 U.S.C. 154(b) by 0 days.

(21) Appl. No.: 14/217,296

(22) Filed: Mar. 17, 2014

(65) Prior Publication Data

US 2014/0343537 A1    Nov. 20, 2014

Related U.S. Application Data

(60) Provisional application No. 61/800,288, filed on May 20, 2013.

(51) Int. Cl.
| | |
|---|---|
| *A61M 25/00* | (2006.01) |
| *B29C 53/36* | (2006.01) |
| *B29C 53/50* | (2006.01) |
| *B29L 31/00* | (2006.01) |
| *B29C 53/38* | (2006.01) |

(52) U.S. Cl.
CPC .... *A61M 25/0045* (2013.01); *A61M 25/0009* (2013.01); *A61M 25/005* (2013.01); *A61M 25/0012* (2013.01); *A61M 2025/0046* (2013.01); *B29C 53/38* (2013.01); *B29C 53/50* (2013.01); *B29L 2031/7542* (2013.01); *Y10T 156/10* (2015.01)

(58) Field of Classification Search
CPC ........ Y10T 156/1036; Y10T 156/1038; A61M 25/0009; A61M 25/0012; A61M 25/0045; A61M 25/005; A61M 2025/0046; B29C 53/38; B29C 53/385; B29C 53/50; B29D 23/001; B29K 2027/18; B29L 2031/7542; B29L 2009/00; B29L 2023/007
See application file for complete search history.

(56) References Cited

U.S. PATENT DOCUMENTS

| | | | |
|---|---|---|---|
| 2,805,973 | A | 9/1957 | Klasing et al. |
| 3,269,278 | A | 8/1966 | Olstad |
| 3,511,435 | A | 5/1970 | Cawley et al. |
| 3,540,959 | A | 11/1970 | Houghton |
| 3,879,516 | A | 4/1975 | Wolvek |
| 4,478,898 | A | 10/1984 | Kato |
| 4,516,972 | A | 5/1985 | Samson |
| 4,636,346 | A | 1/1987 | Gold et al. |
| 4,863,442 | A | 9/1989 | DeMello et al. |
| 5,047,045 | A | 9/1991 | Arney et al. |

(Continued)

FOREIGN PATENT DOCUMENTS

| | | |
|---|---|---|
| WO | 9113648 | 9/1991 |
| WO | 9620750 | 7/1996 |

(Continued)

*Primary Examiner* — Carson Gross
(74) *Attorney, Agent, or Firm* — William A. English; Vista IP Law Group LLP (57) ABSTRACT

Apparatus and methods are provided for making catheters having intermediate layers that minimize or eliminate gaps during layup.

21 Claims, 6 Drawing Sheets

(56) References Cited

U.S. PATENT DOCUMENTS

| | | |
|---|---|---|
| 5,176,661 A | 1/1993 | Evard et al. |
| 5,217,440 A | 6/1993 | Frassica |
| 5,254,107 A | 10/1993 | Soltesz |
| 5,370,655 A | 12/1994 | Burns |
| 5,447,497 A | 9/1995 | Sogard et al. |
| 5,514,236 A | 5/1996 | Avellanet et al. |
| 5,545,511 A | 8/1996 | Hulderman et al. |
| 5,549,109 A | 8/1996 | Samson et al. |
| 5,569,221 A | 10/1996 | Houser et al. |
| 5,599,305 A | 2/1997 | Hermann et al. |
| 5,676,659 A | 10/1997 | McGurk |
| 5,713,867 A | 2/1998 | Morris |
| 5,718,973 A * | 2/1998 | Lewis et al. ............... 623/1.32 |
| 5,735,809 A | 4/1998 | Gorsuch |
| 5,811,043 A | 9/1998 | Horrigan et al. |
| 5,836,926 A | 11/1998 | Peterson et al. |
| 5,967,988 A | 10/1999 | Briscoe et al. |
| 6,004,310 A | 12/1999 | Bardsley et al. |
| 6,027,779 A | 2/2000 | Campbell et al. |
| 6,177,523 B1 | 1/2001 | Reich et al. |
| 6,183,443 B1 | 2/2001 | Kratoska et al. |
| 6,217,566 B1 | 4/2001 | Ju et al. |
| 6,310,244 B1 | 10/2001 | Tran et al. |
| 6,315,792 B1 | 11/2001 | Armstrong et al. |
| 6,338,725 B1 | 1/2002 | Hermann et al. |
| 6,511,462 B1 | 1/2003 | Itou et al. |
| 6,592,576 B2 | 7/2003 | Andrews et al. |
| 6,669,886 B1 | 12/2003 | Willard |
| 6,830,568 B1 | 12/2004 | Kresten et al. |
| 6,837,890 B1 | 1/2005 | Chludzinski et al. |
| 6,942,654 B1 | 9/2005 | Schaefer et al. |
| 6,945,970 B2 | 9/2005 | Pepin |
| 6,946,173 B2 | 9/2005 | Lim et al. |
| 6,979,290 B2 | 12/2005 | Mourlas |
| 7,188,623 B2 | 3/2007 | Anderson et al. |
| 7,273,469 B1 | 9/2007 | Chan et al. |
| 7,306,585 B2 | 12/2007 | Ross |
| 7,691,461 B1 | 4/2010 | Prabhu |
| 2001/0016702 A1 | 8/2001 | Benjamin |
| 2001/0053931 A1 | 12/2001 | Hess et al. |
| 2002/0032370 A1 * | 3/2002 | Kamata et al. ............... 600/140 |
| 2002/0041899 A1 | 4/2002 | Chudzik et al. |
| 2002/0156494 A1 | 10/2002 | Simhambhatla et al. |
| 2003/0233115 A1 | 12/2003 | Eversull et al. |
| 2005/0085841 A1 | 4/2005 | Eversull et al. |
| 2005/0085842 A1 | 4/2005 | Eversull et al. |
| 2005/0149104 A1 | 7/2005 | Leeflang et al. |
| 2005/0197623 A1 | 9/2005 | Leeflang et al. |
| 2005/0228452 A1 | 10/2005 | Mourlas et al. |
| 2007/0043333 A1 * | 2/2007 | Kampa et al. ............... 604/523 |
| 2007/0074805 A1 | 4/2007 | Leeflang et al. |
| 2007/0075452 A1 * | 4/2007 | Leeflang et al. ............... 264/129 |
| 2007/0088296 A1 | 4/2007 | Leeflang |
| 2007/0169877 A1 | 7/2007 | Leeflang |
| 2009/0227962 A1 | 9/2009 | Eversull |
| 2011/0264057 A1 | 10/2011 | Eversull |

FOREIGN PATENT DOCUMENTS

| | | |
|---|---|---|
| WO | 9740880 | 11/1997 |
| WO | 9851370 | 11/1998 |
| WO | 9937350 | 7/1999 |
| WO | 0107101 | 2/2001 |
| WO | 03020353 | 3/2003 |
| WO | 2004075961 | 9/2004 |

* cited by examiner

CATHETERS WITH INTERMEDIATE LAYERS AND METHODS FOR MAKING THEM

RELATED APPLICATION DATA

This application claims benefit of co-pending provisional application Ser. No. 61/800,288, filed Mar. 15, 2013, the entire disclosure of which is expressly incorporated by reference herein.

FIELD OF THE INVENTION

The present invention relates generally to apparatus and methods for making catheters, sheaths, or other tubular devices, and, more particularly, to apparatus and methods for making intermediate layers for and incorporating them into such tubular devices.

BACKGROUND

Catheters are elongate tubular devices sized for introduction into body passages and cavities of a patient, such as a patient's vascular system, gastrointestinal system, abdominal cavity, and the like. A catheter may include one or more lumens intended for passing various other devices, agents, and/or fluids into a body lumen or cavity accessed by the catheter. Catheters are often used to traverse tortuous anatomy and/or and or perform diagnostic or interventional procedures within the body. To perform these functions, catheters often must possess complex functional and mechanical properties. Catheters are often constructed of multiple layers and/or segments in order to achieve desired properties. For example, catheters often comprise an inner layer or liner, a reinforcing layer, such as a metallic coil or braid and an outer layer or jacket. Using conventional methods of construction, adding multiple layers, including intermediate layers may lead to sink, air bubbles, wall thickness irregularities, and/or other undesirable results. Thus, improved devices and methods relating to intermediate catheter layers are needed.

SUMMARY

The present invention is directed to catheters, sheaths, or other tubular devices including multiple layers. More particularly, the present invention is directed to devices having at least on intermediate layer and constructions and methods relating to intermediate layers for improving catheter performance and consistency.

In one embodiment, a tubular body is provided that includes a proximal end, a distal end sized for introduction into a body lumen, and has at least three concentric layers including at least one intermediate layer where the intermediate layer comprises at least one inner and one outer layer bonded to one another and the inner layer is capable of heat bonding to an underlying layer, and the outer layer is capable of heat bonding to an overlying layer.

In another embodiment, a tubular body is provided that is sized for introduction into a body lumen having at least three concentric layers, including at least one intermediate layer, where the intermediate layer comprises at least one seam extending substantially between the ends of the catheter.

In another embodiment, a method is provided for constructing a tubular body sized for introduction into a body lumen that includes the steps of providing a strip of material comprising longitudinal edges extending between end of the catheter; positioning the strip around one or more underlying layers to form an intermediate layer; directing one or more layers around the strip; and heating the sub-assembly to bond the various layer layers and the strip.

BRIEF DESCRIPTION OF THE DRAWINGS

The drawings illustrate exemplary embodiments of the invention, in which.

DETAILED DESCRIPTION OF THE EXEMPLARY EMBODIMENTS

Figure 1:
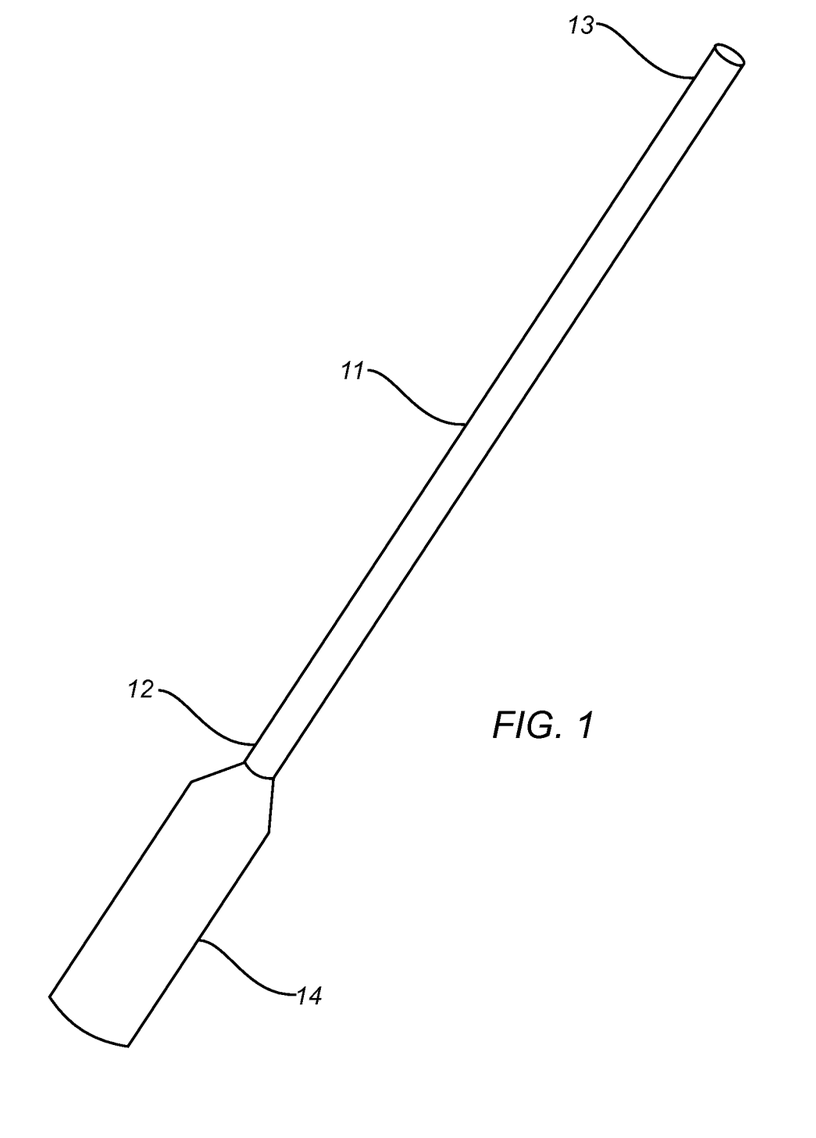
FIG. 1 is a perspective view of an exemplary embodiment of a catheter.

Turning to the drawings, FIG. 1 shows a tubular device 11 designed for accessing a body lumen or cavity, e.g., a catheter, including a distal end 13, a proximal end 12, an elongate body there between, and a hub 14. The catheter 11 may comprise one or more lumens and may be constructed of one or more layers (e.g., layered radially) and/or segments (e.g., segmented axially), typically being constructed of multiple layers and multiple segments to impart multiple desired properties throughout the device. The hub 14 may include one or more valves, side ports, actuators, passages, connectors, etc. as are known in the art.

Figure 2:
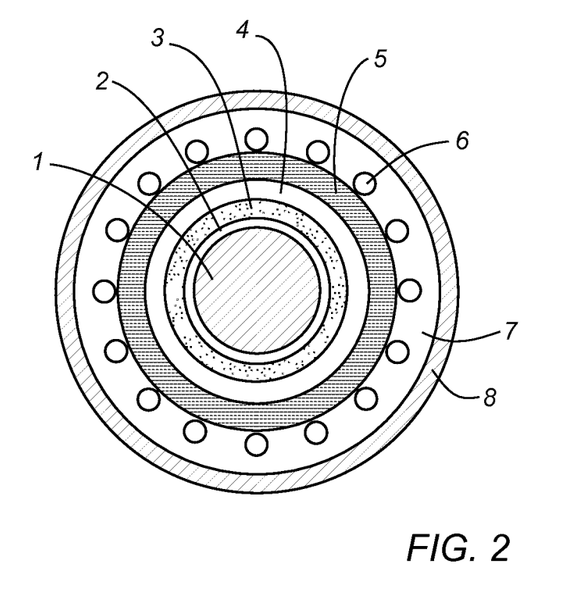
FIG. 2 is a cross-sectional view showing a catheter layup.

Turning to FIG. 2, a catheter layup is illustrated including a mandrel 1, and a series of generally concentric layers, including an inner layer 3, an intermediate layer 5, a reinforcing layer 6, and outer layer 8. In order to achieve desired mechanical, physical, and/or performance properties, each of the layers may comprise a different material and/or one or more longitudinal segments. For example, the inner layer 3 may comprise a fluoropolymer, e.g., PTFE, FEP, ETFE, etc., in order to create a lubricious interface for devices sliding through the finished catheter.

Alternatively, the inner layer 3 may be formed from one or more layers of thermoplastic or other polymeric material including one or more coatings on the inner surface having desired properties, e.g., a hydrophilic and/or lubricious coating, e.g., similar to the liners disclosed in U.S. Pat. Nos. 7,550,053 and 7,553,387, and U.S. Publication No. 2009/0126862 the disclosures of which are expressly incorporated by reference herein.

The intermediate layer 5 may comprise a material capable of adhering to both the inner layer 1 and the reinforcing layer 6 and/or outer layer 8. This may be particularly important when the inner layer 1 comprises a fluoropolymer and/or other lubricious materials, such as PTFE, FEP, or ETFE, PE, HDPE, etc., which generally resists bonding. More generally, an intermediate layer 5 may be used to bridge any incompatibilities between two or more adjacent layers, be they related to melt-flow, bonding, adherence, chemical, or other properties. Moreover, intermediate layers may be used for other purposes, such as providing insulation (e.g., electrical, thermal, chemical, etc.), for modulating mechanical properties, for isolation of material from direct body contact, as a reservoir for drugs or other substances, e.g., to facilitate elution over time, and/or to increase tensile strength, burst pressure, or otherwise improve mechanical characteristics. The reinforcing layer 6 may comprise braid, coil, mesh, axial elements, and the like.

Figure 3:
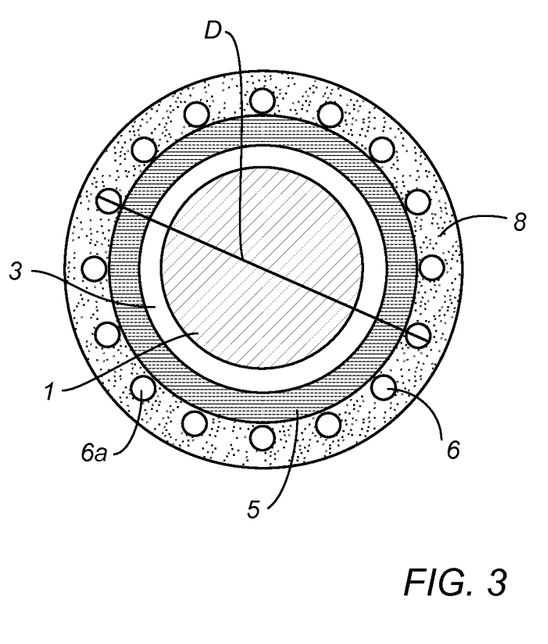
FIG. 3 is a cross-sectional view after reflow of the catheter layup of FIG. 2.

As is known in the art, the layup of FIG. 2 may be ultimately heated, reflowed, laminated, and/or bonded to create a composite tubular catheter as exemplified by FIG. 3. The mandrel 1 may be subsequently removed, leaving a central lumen. While construction of a tubular device having a single central lumen is illustrated, a catheter may be envisioned and similarly constructed comprising multiple lumens, each comprising one or more layers and joined to create a single multi-lumen profile.

While FIG. 2 illustrates four principal layers, it may be envisioned that additional layers may be added to the layup, including multiple intermediate and/or reinforcing layers.

Figure 2A:
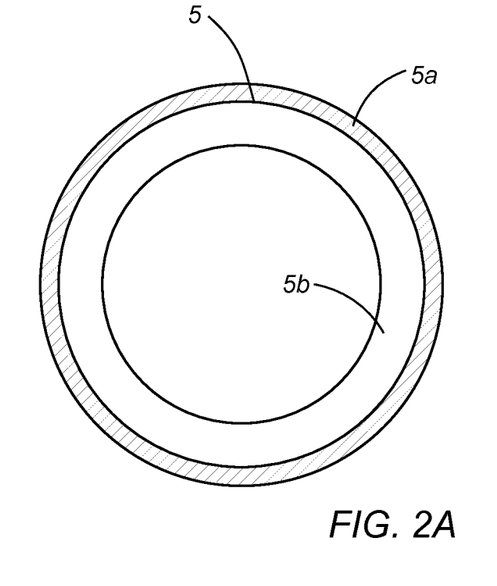
FIGS. 2A and 2B are cross-sectional views showing detailed construction of alternate embodiments of an intermediate layer.
Figure 2B:
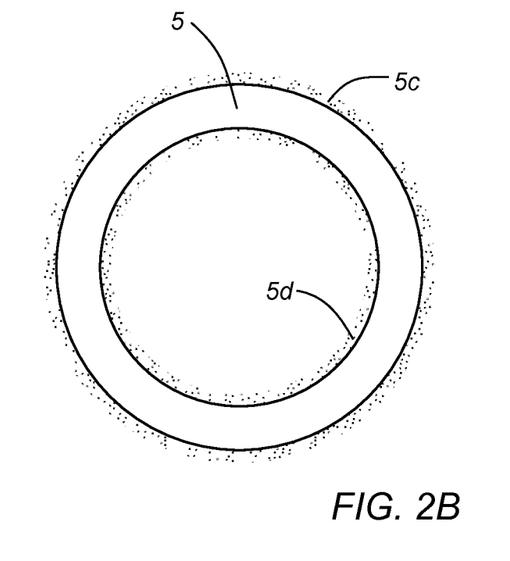

With continued reference to FIG. 2 and returning to the intermediate layer 5, it may be optimized to accomplish adherence of the inner layer 3 to overlying layers. For example, the intermediate layer may comprise Plexar, Orevac, low durometer and/or tacky thermoplastics, such as poly-ether block amide, polyurethane, heat and/or pressure activated adhesives, and the like. Moreover, the intermediate layer 5 may comprise multiple layers as exemplified in FIG. 2A. For example, the intermediate layer 5 may comprise an outer layer 5a and inner layer 5b, which adhere well to one another, while each adheres well to its respective adjacent layer. Alternatively, as shown in FIG. 2B, one or more coatings and/or adhesives 5c, 5d may be applied to the inner and/or outer surface of the intermediate layer 5, e.g., to improve adherence to adjacent layers.

Returning to FIG. 2, layers 3, 5, and 8 generally comprise uninterrupted tubular bodies. Thus, for assembly purposes, the inner diameter of each successive layer must be larger than the outer diameter of the combined components and/or layers below it. Otherwise, each successive layer cannot readily slide over underlying components and/or layers for any substantial length. Accordingly, an inner gap 2 is illustrated between the mandrel 1 and the inner layer 3, an intermediate gap 4 is illustrated between the inner layer 3 and the intermediate layer 5, and an outer gap 7 is illustrated between the intermediate layer 5 and the reinforcing and outer layers 6, 8. The gap required to facilitate assembly depends on respective material properties of adjacent layers, including coefficient of friction and dimensional tolerances. Typically, functional gap sizes may range from 0.002 to 0.010 inch (0.05-0.25 mm). Smaller gaps are often infeasible due to dimensional tolerances, material compliance, and/or coefficient of friction. Larger gap sizes may be required in certain situations, for example, in the setting of large diameters, thin walls, high compliance, and/or high coefficient of friction.

Again returning to FIG. 3, after the layup is completed, the layers are typically heated, compressed, and/or laminated (e.g., reflowed) to create a tubular catheter. As is known in the art, heat shrink tubing, not shown, is often used for this purpose, although dies and/or other means of combined compression and heating may be used. It will be appreciated that gaps shown in FIG. 2. are no longer present. In general, layers above gaps are comprised of melt-flowable materials such that, when heated, the material flows into and fills the underlying gap. Accordingly, the finished diameters of each melt-flowable layer of the catheter will generally be less than the starting diameters of that layer. The inner diameter of the catheter is generally defined by the mandrel 1, and the cross-sectional area of each layer is conserved despite changes in diameter.

Because the inner lumen is intended to be open, the inner most layer may be acceptably comprised of a non-melt-flowable material, for example, PTFE.

With further reference to FIGS. 1 and 3, it may be appreciated that the reinforcing layer 6 may rest generally directly upon the intermediate layer 5. This may be accomplished by applying the reinforcing layer 6 to a layup sub-assembly (not shown) comprising only the intermediate layer 5 and all underlying layers/components. For example, it is possible to braid or coil directly onto such a layup sub-assembly. Alternatively, a discrete length of braid or coil may be applied to such a layup sub-assembly and then reduced in diameter to fit tightly over intermediate layer 5, for example by elongating a segment of braid, or twisting a segment of coil. It will be appreciated that the diameter D of the reinforcing layer 6 cannot easily be and generally does not change during reflow, such that the diameter of the reinforcing layer 6 at the lay-up stage as shown (but not labeled) in FIG. 2 is the same as in the finished catheter as shown in FIG. 3. Due to underlying gaps, the cross-section of the intermediate layer 5 moves inward and away from the reinforcing layer 6 during reflow and the cross-section of the outer layer 8 moves also inward and into the reinforcing layer 6, e.g. creating sink. In some cases, this may not be desirable, for example it may lead to surface exposure of the reinforcing layer 6 and/or and may necessitate using a thicker outer layer 8. Thus, creating a very thin walled catheter may be difficult. Furthermore, the diameter D of the reinforcing layer 6 shown in FIG. 5 may be generally made smaller than the diameter D of the reinforcing layer 6 shown in FIG. 3 for the same general catheter construction. This may be desirable to achieve certain mechanical properties, dimensional requirements, and the like.

In order to eliminate or minimize sink and/or minimize the diameter of the reinforcing layer 6, as described above, or sink more generally, elimination or substantial elimination of gaps between layers during layup may be desirable. Furthermore, presence of gaps in the initial layup may cause undesirable air pockets and/or voids during reflow. Furthermore, gaps may lead to cross-sectional irregularities due to differential flow of material during reflow.

Gaps may be eliminated in several ways. For example, the catheter may be subjected to multiple reflow steps, e.g., at multiple stages in the layup. For example, a partial layup may comprise an inner layer and intermediate layer only. Subsequently, the intermediate layer may be flowed down onto the inner layer, for example, using heat shrink. This may substantially eliminate the gap between the inner layer and intermediate layer, and reduce the overall diameter of the sub-assembly. Subsequent layers, including additional intermediate layers, may then be added and additional reflow steps performed as needed.

Alternatively, an intermediate layer may be directly extruded/co-extruded onto layers below it without the presence of a gap.

Figure 4:
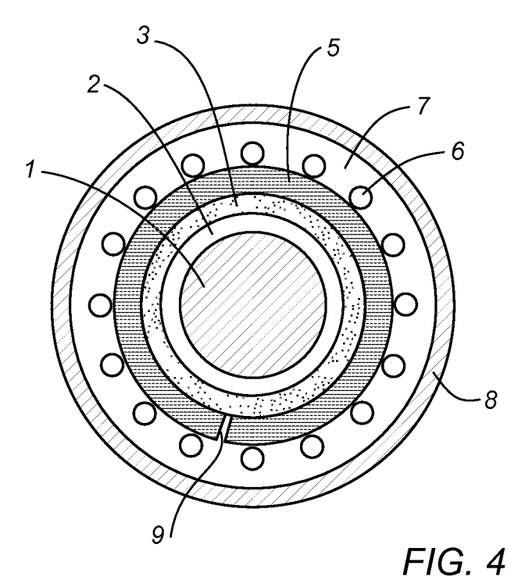
FIG. 4 is a cross-sectional view showing a catheter layup including an interrupted intermediate layer.

Further alternatively, turning to FIG. 4, an intermediate layer 5 may further comprise an interruption 9 along its length, thus allowing it to be placed over underlying layers without difficulty, but eliminating the gap between the intermediate layer 5 and the adjacent inner layer 3. The intermediate layer 5 may comprise a thin strip of material or a tubular layer that has been slit or otherwise interrupted. The interruption 9 may extend substantially axially or helically along the length of the catheter.

Figure 5:
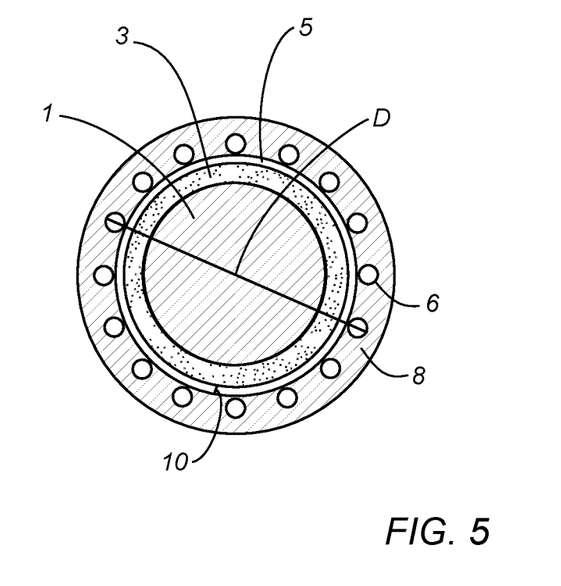
FIG. 5 is a cross-sectional view after reflow of the catheter layup of FIG. 4, including an intermediate layer comprising a seam.

FIG. 5 shows the layup of FIG. 4 after reflow. The edges of the interruption 9 are now closely approximated and/or joined creating a seam 10 extending along the length of the intermediate layer 5.

It can be appreciated that the position of the reinforcing layer 6 remains more substantially constant with respect to the intermediate layer 5. By contrast, sink due to underlying gaps may cause a change in the final position of the reinforcing layer with respect to the intermediate layer, as partially illustrated in FIG. 3 (see, for example, element 6a of reinforcing layer 6).

Other layers of the catheter may be similarly constructed, including an interruption/seam, in order to facilitate a tight fit. Such tight fitting layers may comprise any materials generally used in catheter construction, e.g., polyether block amide, polyamide, polyurethane, PEEK, HDPE, PET, polyimide, polyethylene, HDPE, PVC, polypropylene, other engineering plastics, fluoropolymers, and the like. Tight fitting layers may more readily conform to non-melt-flowable materials, PTFE for example, by eliminating the need to fill an underlying gap.

Multiple tight fitting layers may be used in catheter construction. Such layers may comprise multiple segments along their length, for example, multiple Durometers of material. Such layers may also be very thin and/or flimsy, which would otherwise present difficulty during assembly, e.g., it is difficult to slide a thin walled low Durometer tube over a catheter assembly during layup.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for constructing a tubular body sized for introduction into a body lumen comprising the steps of:
   providing a strip of material comprising longitudinal edges extending between first and second ends;
   positioning the strip around one or more underlying layers to form an intermediate layer having an interruption extending between the first and second ends;
   after positioning the strip around the one or more underlying layers to form the intermediate layer, directing one or more outer layers around the strip and the one or more underlying layers to provide a sub-assembly; and
   heating the sub-assembly to bond the one or more outer layers and underlying layers and the strip.

2. A method for constructing a tubular body sized for introduction into a body lumen, the tubular body comprising proximal and distal ends and a length between the proximal and distal ends, the method comprising:
   providing a liner surrounding a mandrel along the length;
   wrapping an intermediate layer around the liner and mandrel, the intermediate layer comprising an interruption extending along the length such that the intermediate layer is wrapped tightly around the liner to substantially eliminate a gap between the intermediate layer and the liner;
   after wrapping the intermediate layer around the liner and mandrel, applying a reinforcing layer around the intermediate layer;
   applying a continuous outer layer around the reinforcing layer to provide an assembly;
   heating the assembly to bond the layers together; and
   removing the mandrel, thereby providing an open central lumen along the length.

3. The method of claim 2, wherein wrapping the intermediate layer comprises wrapping the intermediate layer around the liner such that longitudinal edges defining the interruption are positioned adjacent one another without overlapping one another.

4. The method of claim 3, wherein the longitudinal edges reflow together to define a seam when the assembly is heated.

5. The method of claim 3, wherein the longitudinal edges extend substantially axially along the length.

6. The method of claim 3, wherein the longitudinal edges extend helically along the length.

7. The method of claim 2, wherein the reinforcing layer comprises a braid or coil that is wrapped around the intermediate layer after wrapping the intermediate layer around the liner and mandrel.

8. The method of claim 7, wherein heating the assembly comprises reflowing at least the intermediate layer and the outer layer, and wherein a position of elements of the braid or coil remain substantially constant during heating.

9. The method of claim 2, wherein the liner comprises a fluoropolymer.

10. The method of claim 2, wherein the liner is formed from polytetrafluoroethylene (PTFE) or fluorinated ethylene propylene (FEP).

11. The method of claim 2, wherein the intermediate layer comprises a strip that is wound around the liner and mandrel.

12. The method of claim 11, wherein the strip is formed by slitting a tubular layer of material.

13. The method of claim 2, wherein the intermediate layer comprises inner and outer layers, the inner layer configured to adhere to the liner and the outer layer configured to adhere to the continuous outer layer.

14. The method of claim 2, wherein the intermediate layer comprises inner and outer surfaces, the inner surface comprising a coating or adhesive configured to adhere to the liner and the outer surface comprising a coating or adhesive configured to adhere to the continuous outer layer.

15. The method of claim 2, wherein the intermediate layer has a thickness that is thinner than a thickness of any of the other layers of the assembly.

16. The method of claim 4, wherein the intermediate layer comprises a tacky thermoplastic.

17. The method of claim 2, wherein the intermediate layer has a durometer that is lower than a durometer of any of the other layers of the assembly.

18. A method for constructing a tubular body sized for introduction into a body lumen, the tubular body comprising a length between proximal and distal ends thereof, the method comprising:

provding a liner surrounding a mandrel along the length, the liner comprising a fluoropolymer;

wrapping an intermediate layer around the liner and mandrel, the intermediate layer comprising a tacky thermoplastic material including an interruption defined by longitudinal edges extending along the length such that the intermediate layer is wrapped tightly around the liner to substantially eliminate a gap between the intermediate layer and the liner and the longitudinal edges are disposed adjacent one another;

after wrapping the intermediate layer around the liner and mandrel, applying a braid or coil around the intermediate layer to provide a reinforcing layer;

after applying a braid or coil around the intermediate layer, applying a continuous outer layer around the reinforcing layer to provide an assembly; and heating the assembly to reflow at least the intermediate layer and the outer layer to bond the layers together and form a tubular body, and wherein a position of elements of the braid or coil remain substantially constant during reflow.

19. The method of claim 18, wherein the longitudinal edges reflow together to define a seam when the assembly is heated.

20. The method of claim 19, wherein the longitudinal edges extend helically or substantially axially along the length.

21. The method of claim 1, wherein directing one or more outer layers around the strip and the one or more underlying layers to provide a sub-assembly comprises:

braiding or coiling a plurality of reinforcing elements around the strip and the one or more underlying layers; and placing an uninterrupted tubular body around the reinforcing elements.

* * * * *